United States Patent [19]

Fridd et al.

[11] Patent Number: 4,898,595
[45] Date of Patent: Feb. 6, 1990

[54] COLORING KERATINOUS MATERIAL

[75] Inventors: Petrina F. Fridd; Rosemary M. Taylor, both of Wales, United Kingdom

[73] Assignee: Dow Corning Limited, Barry, Wales

[21] Appl. No.: 15,185

[22] Filed: Feb. 17, 1987

[30] Foreign Application Priority Data

Feb. 26, 1986 [GB] United Kingdom ............... 8604705
Jan. 12, 1987 [GB] United Kingdom ............... 8700620

[51] Int. Cl.$^4$ .......................... A61K 7/06; A61K 7/13
[52] U.S. Cl. ............................................. 8/405; 8/406; 132/202; 132/208; 424/70
[58] Field of Search ................ 132/7, 202, 208; 424/70; 8/405, 406

[56] References Cited

U.S. PATENT DOCUMENTS

| 3,964,500 | 6/1976 | Drakoff | 424/81 |
| 4,423,032 | 12/1983 | Abe et al. | 424/70 |
| 4,487,883 | 12/1984 | Homan | 525/437 |
| 4,490,356 | 12/1984 | Sebag et al. | 8/406 |
| 4,563,347 | 1/1986 | Starch | 132/7 |

FOREIGN PATENT DOCUMENTS

| 192310 | 11/1982 | Japan | 8/405 |
| 2039512 | 8/1980 | United Kingdom . | |
| 2131821 | 6/1984 | United Kingdom . | |
| 2138845 | 10/1984 | United Kingdom . | |
| 2143434 | 2/1985 | United Kingdom . | |
| 2157168 | 10/1985 | United Kingdom . | |
| 2164558 | 3/1986 | United Kingdom . | |
| 2173515 | 10/1986 | United Kingdom . | |

Primary Examiner—Paul Lieberman
Assistant Examiner—Linda D. Skaling
Attorney, Agent, or Firm—Marc C. Pawl

[57] ABSTRACT

The specification discloses a process for coloring hair in which certain polysiloxanes including siloxane units having a silicon bonded hydroxy group are employed to provide improved depth of color or color retention. Preferably the polysiloxanes are employed as a treatment on hair prior to or after application of colorant.

12 Claims, No Drawings

COLORING KERATINOUS MATERIAL

The present invention is concerned with colouring keratinous material and is particularly concerned with colouring human hair.

Human hair comprises fibres which have a layer of flat scales pointing outward from root to tip. Although the individual scales are thin, they are long and overlap each other forming a continuous, multilayered shield around the fibre. Within this shield lies hair cortex which constitutes the bulk of the hair Dispersed throughout the cortex are pigment particles called melanin Their number and distribution pattern determine the hair colour Hair is composed almost entirely of keratin i.e. cystine-containing proteins. It is understood that the two main protein fractions are low- and high-sulphur proteins. The low-sulphur fraction consists of proteins of high molecular weight and high degree of molecular organization (α-helical) whereas the high-sulphur proteins are of low molecular weight and do not exhibit any regular secondary structure. Both proteins participate in a composite filament-matrix texture which is the dominant structural element of hair cortex. The filaments are composed of low-sulphur proteins and the surrounding matrix is made up of high-sulphur proteins. The chemical composition of the scales differs from that of the fibre and scale cells do not apparently contain any low-sulphur proteins. The exposed portion of each scale is heavily cross-linked by cystine and this fact, in conjunction with the multilayered shield effect, makes the scales a formidable barrier to penetration by chemicals to the interior of the hair fibre.

It is a practice to modify the colour of human hair by the use of hair colorants containing dyes. These hair colorants may be divided conveniently into those which give "permanent", "semi-permanent" or "temporary" results. By "permanent" is meant that the result of the colouring process remains fast to the action of shampoos, perspiration, sunlight and mechanical abrasion until the hair grows out. By "semi-permanent" is meant that the result of the colouring process remains fast to the action of shampoos, perspiration, sunlight and mechanical abrasion for approximately 6 to 10 washings with shampoo. By "temporary" is meant that the result of the colouring process may be removed in from one to three shampooings.

In permanent hair colorants the dyes used (at least until recent years) have been predominantly of the oxidation type whereby a water insoluble coloured material is produced inside the hair fibre as a result of oxidation of colourless intermediates which penetrate the cortex. The colour forming reactions are accomplished by primary intermediates, secondary intermediates and oxidants. Primary intermediates include for example p-phenylenediamine, p-toluenediamine, p-aminodiphenylamine and o,p-aminophenol, p-amino-o-cresol, toluene Z, 5 diamine, N-phenyl-p-phenylenediamine, pyrogallol, 4,4-diaminodiphenylene-diamine, p-methylaminophenol, o-phenylenediamine, toluene 3, 4 diamine, p-chloro-o-phenylenediamine, o-chloro-p-phenylenediamine and Z, 6 diaminopyridine. The secondary intermediates, also known as couplers or modifiers, are used in conjunction with the primary intermediates to produce dyes. Secondary intermediates include for example m-aminophenol, resorcinol, m-phenylenediamine, hydroquinone, resorcine, toluene 2, 4 diamine, 1-naphthol, 4-methoxy-m-phenylene-diamine or α-naphthol and polyhydroxyphenols. It is believed that the initial oxidation product of p-phenylenediamine for example is benzoquinone diimine. It may react with p-phenylenediamine to form a dye but the diimine reacts much faster with secondary intermediates to form a variety of dyes. By selection of appropriate intermediates, various colours may be achieved. The oxidant (otherwise known as the developer) e.g. hydrogen peroxide, sodium perborate, urea peroxide or sodium percarbonate, is usually mixed with the dye intermediates just before use. In addition to its function in relation to the dye intermediates hydrogen peroxide may exert some influence on the colouring of the hair by bleaching the melanin. Autoxidative dyes have also been proposed with a view to avoiding addition of separate oxidant.

It is a practice to include in permanent hair colorants nitro dyes which dye the hair without oxidation e.g. nitro derivatives of aminophenols and benzenediamines, for example nitro-p-phenylenediamine, p-nitro-o-phenylenediamine, 4-nitro-o-phenylenediamine,2-amino-4-nitrophenol, 2-amino-5-nitrophenol, picramic acid, 1,4 diaminoanthraquinone and picric acid. The nitro dyes and also anthraquinone dyes and azobenzene dyes are also commonly used for semi-permanent hair colorants. For example nitrophenylene diamines and nitroaminophenols provide a range of yellow, orange, red and violet colours and aminoanthraquinones provide blue colours. Dyestuffs which may be employed for permanent or semi-permanent hair colorant systems also include for example plant hair dyes, for example those derived from henna, walnut or soybean and metallic hair dyes for example those which employ insoluble salts of for example iron, copper, lead, manganese, nickel or cadmium.

It is a practice to include in permanent and semi-permanent hair colorant compositions not only water and the dye or dye intermediates but also surfactants (to enhance wetting, cleansing, spreading and viscosity control) for example ammonium oleate, alkanolamides, fatty alkyl sulphates, thickeners for example carboxy methyl cellulose, materials to promote diffusion of the dye into hair and materials for solubilizing the dyes. Conditioning agents may also be included.

Temporary hair colorants make use of generally higher molecular weight dyes which do not penetrate the hair structure significantly but rather become deposited on the surface. Dyestuffs which may be employed for temporary hair colorant systems include oxidation dyes, azo dyes, quinoline dyes, acridine dyes, azine dyes, oxazine dyes, indigoid dyes, anthraquinone dyes, stilkene dyes and thiazole dyes. Temporary hair colorant systems may also employ pigments, for example iron oxides, titanium dioxide or carbon black and may employ a binder, for example methacrylate, acrylate, vinylacetate or vinylpyrrolidone polymers or copolymers to assist in binding the hair colorant to the hair, together with dispersion media for example water, acetone, ionic or non-ionic surface active agents, lower alcohols, polyhydric alcohols, higher alcohols, fatty acids and liquid hydrocarbons with a view to ease of application of the colorant and desired texture of the coloured hair.

It is a practice in the care of human hair to apply so-called conditioner compositions with a view to enhancing desired qualities of the hair for example ease of combing, detangling, body, shine, texture, split end mending, prevention of static build up and general manageability. It has been proposed to include in conditioner compositions various silicone products, including for example emulsions of the amino silicone polymer amodimethicone. E.P. No. 95 238 discloses materials intended for use as a conditioner for application to hair after shampooing and comprising preferably inter alia certain siloxanes including siloxane units having certain amine, carboxylic, amido groups or quaternised amino groups. It has been for several years the normal practice to apply conditioner compositions, which may include for example one or more silicone polymers, to the hair after the operation of colouring the hair has been completed.

We have now found that an improvement in the depth of colour of keratinous material treated with a hair colorant system and in the number of washings through which the colour is retained by the material may be enhanced when certain hydroxyfunctional silicones are employed in conjunction with the colorant system.

The present invention provides, in one of its aspects, in a method of colouring keratinous material by means of a hair colorant system, the improvement which comprises the use of a polysiloxane comprising at least one siloxane unit having the general formula $$R_a(HO)SiO_{\frac{(3-a)}{2}} \quad (i)$$

in which each R represents a monovalent hydrocarbon group having 1 to 12 inclusive carbon atoms, or an alkoxy or alkoxyalkoxy group, in which each alkoxy group has up to 7 carbon atoms and a has the value 1 or 2, any other siloxane units of the polysiloxane being of the general formula $$Z_cSiO_{\frac{(4-c)}{2}} \quad (ii)$$

in which each Z represents a monovalent hydrocarbon group having 1 to 12 inclusive carbon atoms, or an alkoxy or alkoxyalkoxy group in which each alkoxy group has up to 7 carbon atoms and c has the value 0, 1, 2 or 3 to enhance the depth of colour and/or prolong retention of colour imparted to the hair by the colorant system.

The invention also provides a method of colouring keratinous material comprising the steps of applying a hair colorant system to the material and applying before, during or after application of the colorant system a polysiloxane comprising at least one siloxane unit having the general formula $$R_a(HO)SiO_{\frac{(3-a)}{2}} \quad (i)$$

in which each R represents a monovalent hydrocarbon group having 1 to 12 inclusive carbon atoms, or an alkoxy or alkoxyalkoxy group, in which each alkoxy group has up to 7 carbon atoms and a has the value 1 or 2, any other siloxane units of the polysiloxane being siloxane units of the general formula $$Z_cSiO_{\frac{(4-c)}{2}} \quad (ii)$$

in which each Z represents a monovalent hydrocarbon group having 1 to 12 inclusive carbon atoms, or an alkoxy or alkoxyalkoxy group, in which each alkoxy group has up to 7 carbon atoms and c has the value 0, 1, 2 or 3.

The polysiloxanes are characterised by the presence of at least one silicon-bonded hydroxyl group. Depending on the value of a, the siloxane units (i) may be present in the polysiloxane as terminal units or as linking units of the polymer or both and may provide any desired proportion of the total siloxane units in the polymer, provided at least one SiOH group is present. Preferably siloxane units (i) provide from about 0.1 to about 20 percent, more preferably 1 to 5 percent of the total siloxane units. However, they may if desired provide 100 percent of the total units in the polysiloxane. Any remaining siloxane units of the polysiloxane are those according to the general formula (ii).

In units (i) and (ii) each R and each Z may be, for example, an alkyl group having 1 to 6 carbon atoms for example methyl, propyl or butyl, or an aryl group, for example phenyl, or an unsaturated aliphatic or alicyclic group, for example vinyl or cyclohexenyl, or an alkoxy or alkoxyalkoxy group having less than 7 carbon atoms, for example methoxy, ethoxy, propoxy or methoxyethoxy. Preferably the R and Z substituents are selected from alkyl or alkoxy groups having from 1 to 4 inclusive carbon atoms and phenyl groups. The value of c may be 0, 1, 2 or 3 and thus the units (ii) may provide terminal, main chain or branching units in the polysiloxane.

The polysiloxane may be linear or branched and may have a consistency ranging from a mobile liquid to a resinous material. Good results have been achieved by use of materials having viscosities in the range $2 \times 10^{-5}$ to 1 m$^2$/s. The preferred polysiloxanes are the liquid $\alpha,\omega$ hydroxy polydiorganosiloxanes which have two units of formula (i) in which a has the value 2 and R represents a methyl group, and a plurality of units of formula (ii) in which c has the value 2. Conveniently each Z represents a methyl group. Preferred polysiloxanes are according to the average formula $$HO(R_2SiO)_nH$$

where each R represents a methyl group and n has a value in the range 600 to 1700. The polysiloxane is preferably applied to the hair or other keratinous material as an aqueous emulsion of fine particle size.

In a method according to the invention the polysiloxane may provide the sole polysiloxane employed in the method. However, other polysiloxanes may also be present if desired. For example when further enhancement of durability of the colour on the hair is desired, it is sometimes possible to achieve this by employing, in addition to the polysiloxane as aforesaid, a polysiloxane having silicon-bonded hydroxyl and/or alkoxy groups together with silicon-bonded groups having active amino groups, for example, groups such as $\equiv Si(CH_2)_3NH_2$ and $\equiv SiCH_2CH_2NH(CH_2)_3NH_2$. Such amino-containing polysiloxanes are known and include, for example, amodimethicone.

In a method according to the invention the hair colorant system may be any of those conventionally used for the temporary, semi-permanent or permanent colouring of hair as referred to above. The hair colorant system may conveniently comprise water based anionic, nonionic or cationic emulsions and may include usual additives as referred to above. Various commercially available hair colorant systems may be employed in a method according to the invention, for example those supplied by Elida Gibbs, Bristol Myers and Clairol under the trade names Harmony, Glints and Clairol respectively.

In a method according to the invention the polysiloxane may be applied to the keratinous material in admixture with the colorant system, but it is preferably applied before or after application of the colorant system for example in a shampoo used on the keratinous material before application of the colorant system, or in a conditioner rinse applied to the keratinous material after application of the colorant system.

A method for colouring hair according to the invention may be carried out for example by first washing the hair using a conventional shampoo formulation comprising for example about 20% by weight sodium laurylethersulphate, rinsing with water, drying to the towel dry stage as by padding it to a substantially dry condition and thereafter applying the chosen polysiloxane in aqueous emulsion to the hair whilst the hair is in this substantially dry condition. The hair, after about one minute, may be brought again to the towel dry stage and the colorant system applied and left in place for about 15 to 20 minutes. The hair may then be rinsed to remove residual colouring matter and dried by forced hot air treatment.

A method according to the invention may be employed in the colouring of virgin hair, or in the colouring of hair which has become damaged e.g. as a result of bleaching or of permanent waving, to provide the hair with an enhanced depth of colour. Using the preferred polysiloxanes one may also achieve a prolonged retention of the imparted colour as compared with other methods.

There now follows a description of examples of the invention. In the examples, the symbol Me represents the methyl group. All proportions mentioned in the examples are by weight unless otherwise specified.

In the examples, various commercially available hair colorant systems were used strictly in accordance with their supplier's instructions to colour switches of virgin hair of European origin portions of which had been bleached and portions of which remained unbleached, to provide coloured standard samples of bleached and unbleached virgin hair of each colour. Comparative samples of coloured hair were prepared from similar switches of virgin and bleached virgin hair using control compositions or polysiloxane compositions as a treatment for the commercial hair colorant systems. The colour of the coloured bleached and unbleached portions of the samples was observed and compared with the standard shortly after the colouring operation and, for some samples, after several washes. Except where otherwise specified herein, the various commercially available hair colorant systems used were of the semi-permanent type.

Bleaching of portions of the virgin hair switches was carried out as follows. An end portion of each switch of virgin hair was dipped for two hours at room temperature in a solution formed by mixing equal parts by volume of solutions A and B. Solution A was a 50% by volume aqueous solution of hydrogen peroxide. Solution B was a mixture of 13.5 parts by volume ammonia (sp.gr 0.88) 3 parts by volume Empicol ESB 3 (a sodium lauryl ether sulphate) and 83.5 parts by volume water. After two hours, the hair was removed from the solution, rinsed in running water and then dried using air heated to 70° C.

Control composition 1 was a 0.35% solids aqueous solution of the quaternary ammonium salt cetalkonium chloride. Control composition 2 was a 0.35% solids aqueous solution of a polysiloxane polyoxalkylene copolymer according to the average general formula $Me_3SiO(Me_2SiO)_x(MeR'SiO)_ySiMe_3$ where $R'$ represents $-C_3H_5O(C_2H_4O)_mH$ as supplied by Dow Corning Limited under the trade name Dow Corning 193 Surfactant.

Polysiloxane 1 was an aqueous emulsion of pH of about 7.2 containing 0.35% of a hydroxyl terminated polydimethylsiloxane having the average formula $HO(Me_2SiO)_nH$ in which n has a value of about $1100 \pm 100$.

Polysiloxane 2 was an aqueous emulsion formed from 0.35% of a hydroxyl terminated polydimethylsiloxane of average formula $HO(Me_2SiO)_nH$ in which n has a value of about 20 water and Tergitol TMN6, isolaureth-6, a nonionic surfactant.

In examples 1 and 2 the various hair colorant systems, with and without pretreatment using control compositions and polysiloxanes 1 and 2 were employed to colour switches of bleached and unbleached virgin hair as aforesaid in the following way. The samples produced without pretreatment provided the standard samples and those produced with pretreatment provided the comparative samples. The hair was shampooed using a 20% active sodium laurylether sulphate water based composition. The hair was rinsed and padded dry to a towel dry condition. The selected colorant, made up according to the supplier's instructions was applied to bleached and unbleached portions of the treated hair by covering the hair with the colorant for twenty minutes. The hair was rinsed in running water until the water was colourless. The hair was dried in air heated to 70° C. until the hair became dry. In those cases in which a pretreatment with a control or polysiloxane 1 was employed, after the hair had been padded dry following the initial shampoo and rinse stages, the bleached and unbleached portions of the hair were dipped for one minute in the control composition or the polysiloxane. The hair was removed from the composition and padded dry to a towel dry condition. The selected colorant was then applied to the hair, the hair rinsed and dried as aforesaid. The colour of the bleached and unbleached portions of the samples was observed and compared to that of the standards shortly after the hot air drying step.

EXAMPLE 1

Control compositions 1 and 2 and polysiloxane 1 were evaluated as pretreatments for hair colorant systems using products supplied by Elida Gibbs under the designation Harmony Auburn and Harmony Rich Chestnut using the method described above. Polysiloxane 2 was evaluated using Harmony Auburn. By inspection of the samples coloured with Harmony Rich Chestnut it was found that the depth of colour of the coloured bleached and unbleached portions of the sample made using control composition 2 was the same as the depth of colour of the corresponding portions of the coloured standard, whereas control composition 1 gave slightly more depth of colour on the bleached and unbleached portions than the standard. In comparison, the samples made using polysiloxane 1 had a greater depth of colour on the bleached and unbleached portions than the corresponding portions of the coloured sample made using control composition 1.

By inspection of the samples coloured with Harmony Auburn, it was found that the depth of colour of the coloured bleached and unbleached portions of the samples made using control compositions 1 and Z were similar to each other and greater than the depth of colour of corresponding portions of the standard. In comparison, the sample made using polysiloxane 1 had a greater depth of colour on its bleached and unbleached portions than the corresponding portions of the sample made using control composition 1. In conjunction with Harmony Auburn and in conjunction with Harmony Rich Chestnut, the coloured bleached and unbleached portions of the samples made using polysiloxane 1 showed better depth of colour as compared with the corresponding portions of the standard. Using polysiloxane 2 and Harmony Auburn, some improvement in depth of colour was achieved as compared with the corresponding portions of the standard.

EXAMPLE 2

Switches of bleached and unbleached virgin hair were coloured with Harmony Auburn and Harmony Rich Chestnut with and without pretreatment using polysiloxane 1 and control compositions, using the method described above. The coloured samples were subjected to wash cycles each involving washing the sample in 20% active aqueous solution of sodium lauryl ether sulphate, rinsing with clean water, a second wash in 20% active sodium lauryl ether sulphate, and a second rinse with clean water followed by drying with air heated to 70° C. After each wash cycle each sample was inspected and the colour noted. It was noted that some colour from each sample was washed out. The wash cycles were repeated until the colour on the bleached and unbleached portions of each comparative sample was the same as the colour of the corresponding portion of its washed standard counterpart. The number of wash cycles completed prior to attaining this colour match is shown in the following table:

| Sample Pretreatment | Number of Washes to Match | |
| --- | --- | --- |
| | Auburn | Rich Chestnut |
| Control 1 | 2 | 5 |
| Control 2 | 3 | 0 |
| Polysiloxane 1 | 2 | 7 |

These results indicate that hair samples coloured by a method according to the invention retain their colour through more shampooings than hair coloured without pretreatment using a polysiloxane having units of formula (i).

EXAMPLE 3

Polysiloxanes 1 and 2 were evaluated as post-treatment for hair colorant systems using Harmony Auburn using the method employed for Examples 1 and Z with the exception that no pretreatment was carried out, but a post-treatment was carried out after application of the colorant and after the associated rinsing step.

The coloured hair was padded dry. The post-treatment comprised application to the hair of control composition 1 or a polysiloxane by dipping the coloured hair into the appropriate composition and then drying the hair in air heated to 70° C. A good depth of colour, both on bleached portions of the hair and on unbleached portions, was observed on samples in which polysiloxanes 1 or 2 had been used as post-treatment. This depth of colour was better than those of the corresponding standard counterparts.

EXAMPLE 4

Samples produced as described in Example 3 were subjected to wash cycles and inspections as described in Example 2. The number of wash cycles completed prior to the colour on the bleached and unbleached portions of each comparative sample being the same as the colour of the corresponding portion of its washed standard counterpart is shown in the following table:

| Sample Posttreatment | Number of Washes to Match |
| --- | --- |
| Polysiloxane 1 | 4 |
| Polysiloxane 2 | 1 |

What is claimed is:

1. In a method of coloring keratinous material by means of a hair colorant system, wherein the improvement comprises applying to said keratinous material a polysiloxane comprising from 0.1 to 100% of the total number of siloxane units, siloxane units having the general formula $$R_a(HO)SiO_{(3-a)/2} \quad \text{(i)}$$

wherein R represents a monovalent hydrocarbon group having 1 to 12 inclusive carbon atoms, or an alkoxy or alkoxyalkoxy group, in which each alkoxy group has up to 7 carbon atoms and a is 1 or 2,
the balance of the siloxane units of the polysiloxane having the general formula $$Z_cSiO_{(4-c)/2} \quad \text{(ii)}$$

wherein Z represents a monovalent hydrocarbon group having 1 to 12 inclusive carbon atoms, or an alkoxy or alkoxyalkoxy group in which each alkoxy group has up to 7 carbon atoms and c is 0, 1, 2 or 3,
the resulting polysiloxane having a degree of polymerization in the range of from 600 to 1700.

2. A method according to claim 1 wherein the polysiloxane is a substantially linear material according to the average formula $$HO(R_2SiO)_nH$$

in which R represents an alkyl group having 1 to 6 carbon atoms or a phenyl group and n has a value in the range 600 to 1700.

3. A method according to claim 2 wherein n has a value of about 1100±100.

4. A method according to claim 1 wherein the keratinous material is human hair, the hair is padded to a substantially dry condition, the colorant system applied to the hair whilst in this substantially dry condition and the polysiloxane is applied to the hair in the form of an aqueous emulsion before or after application of the colorant system to the hair.

5. A method according to claim 1, wherein said polysiloxane comprises from 0.1–20% siloxane units of the general formula (i), the balance of the siloxane units having the general formula (ii).

6. A method according to claim 1, wherein said polysiloxane comprises from 1–5% siloxane units of the general formula (i), the balance of the siloxane units having the general formula (ii).

7. In a method of coloring keratinous material comprising the steps of applying a hair colorant system to the keratinous material and applying before, during or after application of the colorant system a polysiloxane comprising from 0.1 to 100% of the total number of siloxane units, siloxane units having the general formula $$R_a(HO)SiO_{(3-a)/2} \quad (i)$$

wherein R represents a monovalent hydrocarbon group having 1 to 12 inclusive carbon atoms, or an alkoxy or alkoxyalkoxy group, in which each alkoxy group has up to 7 carbon atoms and a is 1 or 2,
the balance of the siloxane units of the polysiloxane having the general formula $$Z_c SiO_{(4-c)/2} \quad (ii)$$

wherein Z represents a monovalent hydrocarbon group having 1 to 12 inclusive carbon atoms, or an alkoxy or alkoxyalkoxy group in which each alkoxy group has up to 7 carbon atoms and c is 0, 1, 2 or 3,
the resulting polysiloxane having a degree of polymerization in the range of 600 to 1700.

8. A method according to claim 1 wherein the polysiloxane is a substantially linear material according to the average formula $$HO(R_2SiO)_nH$$

in which R represents an alkyl group having 1 to 6 carbon atoms or a phenyl group and n has a value in the range 600 to 1700.

9. A method according to claim 8 wherein n has a value of about $1100 \pm 100$.

10. A method according to claim 1 wherein the keratinous material is human hair, the hair is padded to a substantially dry condition, the colorant system applied to the dry condition, the colorant system applied to the hair whilst in this substantially dry condition and the polysiloxane is applied to the hair in the form of an aqueous emulsion before or after application of the colorant system to the hair.

11. A method according to claim 7, wherein said polysiloxane comprises from 0.1–20% siloxane units of the general formula (i), the balance of the siloxane units having the general formula (ii).

12. A method according to claim 7, wherein said polysiloxane comprises from 1–5% siloxane units of the general formula (i), the balance of the siloxane units having the general formula (ii).

* * * * *